United States Patent
Edelhauser et al.

(10) Patent No.: US 10,881,433 B2
(45) Date of Patent: Jan. 5, 2021

(54) SOFTWARE FOR USE WITH DEFORMITY CORRECTION

(71) Applicant: Stryker European Operations Holdings LLC, Kalamazoo, MI (US)

(72) Inventors: Adam John Edelhauser, Nyack, NY (US); Ashish Gangwar, Gurgaon (IN); Sandeep Menon, 1st Cross Cooke Town (IN)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 16/218,778

(22) Filed: Dec. 13, 2018

(65) Prior Publication Data

US 2019/0117263 A1    Apr. 25, 2019

Related U.S. Application Data

(63) Continuation of application No. 15/627,900, filed on Jun. 20, 2017, now Pat. No. 10,194,944, which is a
(Continued)

(51) Int. Cl.
*A61B 17/62* (2006.01)
*A61B 17/66* (2006.01)
(Continued)

(52) U.S. Cl.
CPC .............. *A61B 17/62* (2013.01); *A61B 17/66* (2013.01); *A61B 34/10* (2016.02); *A61B 90/37* (2016.02);
(Continued)

(58) Field of Classification Search
CPC ......... A61B 17/60; A61B 17/62; A61B 17/64; A61B 17/6416–6491; A61B 17/66–666;
(Continued)

(56) References Cited

U.S. PATENT DOCUMENTS 5,546,942 A    8/1996  Zhang
5,681,309 A    10/1997 Ross, Jr. et al.
(Continued)

FOREIGN PATENT DOCUMENTS

DE    102006048451 A1    4/2008
EP    2767252 A1    8/2014
(Continued)

OTHER PUBLICATIONS

Craveiro-Lopes, MD, Software Assisted "Ortho-SUV Frame", Int'l Congress on External Fixation & Bone Reconstruction, Oct. 22, 2010.
(Continued)

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

The present disclosure relates to software used in planning the correction of bone deformities preoperatively or postoperatively, and in particular relates to virtually manipulating rings and struts of an external fixation frame in order to plan the steps for making a desired correction to two or more bone portions of a patient. The software can be used prior to surgery, allowing a user to virtually define a bone deformity, and virtually add and manipulate fixation rings and struts to the bone deformity. Based on the virtual manipulations, a correction plan can be generated that describes length adjustments that should be made to the plurality of model struts over a period of time to correct the bone deformity. The software can also be used after surgical fixation of the fixation frame and struts to the deformed bone.

18 Claims, 18 Drawing Sheets

Related U.S. Application Data continuation of application No. 14/926,576, filed on Oct. 29, 2015, now Pat. No. 9,724,129, which is a continuation of application No. 13/770,056, filed on Feb. 19, 2013, now Pat. No. 9,204,937.

(51) Int. Cl.
   *A61B 34/10* (2016.01)
   *A61B 90/00* (2016.01)

(52) U.S. Cl.
   CPC ... *A61B 2034/101* (2016.02); *A61B 2034/104* (2016.02); *A61B 2034/105* (2016.02); *A61B 2090/364* (2016.02); *A61B 2090/376* (2016.02)

(58) Field of Classification Search
   CPC .............. A61B 19/50; A61B 2019/501; A61B 2019/507; A61B 2019/508; A61B 34/00; A61B 2034/101–105; A61B 34/10
   See application file for complete search history.

(56) References Cited

U.S. PATENT DOCUMENTS

| | | | |
|---|---|---|---|
| 5,682,886 A | 11/1997 | Delp et al. | |
| 5,702,389 A | 12/1997 | Taylor et al. | |
| 5,728,095 A | 3/1998 | Taylor et al. | |
| 5,769,092 A | 6/1998 | Williamson, Jr. | |
| 5,824,085 A | 10/1998 | Sahay et al. | |
| 5,880,976 A | 3/1999 | DiGioia, III et al. | |
| 5,891,143 A | 4/1999 | Taylor et al. | |
| 5,971,984 A * | 10/1999 | Taylor | A61B 17/62 128/898 |
| 6,030,386 A * | 2/2000 | Taylor | A61B 17/62 606/54 |
| 6,112,109 A | 8/2000 | D'Urso | |
| 6,129,727 A | 10/2000 | Austin et al. | |
| 6,205,411 B1 | 3/2001 | DiGioia, III et al. | |
| 6,701,174 B1 | 3/2004 | Krause et al. | |
| 6,711,432 B1 | 3/2004 | Krause et al. | |
| 7,039,225 B2 | 5/2006 | Tanaka et al. | |
| 7,280,683 B2 | 10/2007 | Bi et al. | |
| 7,388,972 B2 | 6/2008 | Kitson | |
| 7,394,946 B2 | 7/2008 | Dewaele | |
| 7,547,307 B2 | 6/2009 | Carson et al. | |
| RE40,914 E | 9/2009 | Taylor et al. | |
| 7,837,621 B2 | 11/2010 | Krause et al. | |
| 7,967,868 B2 | 6/2011 | White et al. | |
| 8,055,487 B2 | 11/2011 | James | |
| 8,157,800 B2 | 4/2012 | Vvedensky et al. | |
| 8,257,353 B2 | 9/2012 | Wong et al. | |
| 8,265,949 B2 | 9/2012 | Haddad | |
| 8,296,094 B2 * | 10/2012 | Harrison | B25J 9/1623 702/150 |
| 8,311,306 B2 | 11/2012 | Pavlovskaia et al. | |
| 8,333,766 B2 | 12/2012 | Edelhauser et al. | |
| 8,419,732 B2 | 4/2013 | Mullaney | |
| 8,439,914 B2 | 5/2013 | Ross et al. | |
| 8,484,001 B2 | 7/2013 | Glozman et al. | |
| 8,617,171 B2 | 12/2013 | Park et al. | |
| 8,654,150 B2 | 2/2014 | Haskell | |
| 8,715,291 B2 | 5/2014 | Park et al. | |
| 8,731,885 B2 | 5/2014 | Iannotti et al. | |
| 8,737,700 B2 * | 5/2014 | Park | A61B 5/055 382/128 |
| 8,777,946 B2 | 7/2014 | Lindahl et al. | |
| 8,860,753 B2 | 10/2014 | Bhandarkar et al. | |
| 8,864,750 B2 | 10/2014 | Ross et al. | |
| 8,864,763 B2 | 10/2014 | Murray et al. | |
| 8,923,590 B2 | 12/2014 | Chen et al. | |
| 8,945,128 B2 | 2/2015 | Singh et al. | |
| 8,952,986 B2 | 2/2015 | Haskell | |
| 9,101,398 B2 * | 8/2015 | Singh | A61B 17/62 |
| 9,204,937 B2 | 12/2015 | Edelhauser et al. | |
| 9,524,581 B2 | 12/2016 | Haskell | |
| 9,724,129 B2 | 8/2017 | Edelhauser et al. | |
| 9,788,861 B2 * | 10/2017 | Murray | A61B 17/62 |
| 10,082,384 B1 * | 9/2018 | Singh | A61B 17/62 |
| 10,154,884 B2 | 12/2018 | Kumar et al. | |
| 10,251,705 B2 | 4/2019 | Kumar et al. | |
| 10,258,377 B1 * | 4/2019 | Lavi | A61B 34/10 |
| 2002/0010465 A1 * | 1/2002 | Koo | A61B 17/62 606/57 |
| 2003/0191466 A1 * | 10/2003 | Austin | A61B 17/62 606/54 |
| 2004/0039259 A1 * | 2/2004 | Krause | A61B 17/025 600/300 |
| 2004/0068187 A1 * | 4/2004 | Krause | A61B 17/15 600/443 |
| 2004/0073211 A1 | 4/2004 | Austin et al. | |
| 2004/0073212 A1 | 4/2004 | Kim | |
| 2005/0004451 A1 | 1/2005 | Vilsmeier et al. | |
| 2005/0054917 A1 * | 3/2005 | Kitson | A61F 2/30942 600/427 |
| 2005/0215997 A1 | 9/2005 | Austin et al. | |
| 2005/0267360 A1 | 12/2005 | Birkenbach et al. | |
| 2006/0015120 A1 | 1/2006 | Richard et al. | |
| 2006/0079745 A1 | 4/2006 | Viswanathan | |
| 2006/0161052 A1 | 7/2006 | Colombet et al. | |
| 2006/0189842 A1 | 8/2006 | Hoeg et al. | |
| 2006/0276786 A1 * | 12/2006 | Brinker | A61B 17/62 606/54 |
| 2007/0055234 A1 * | 3/2007 | McGrath | A61B 17/62 606/56 |
| 2007/0078678 A1 | 4/2007 | DiSilvestro et al. | |
| 2007/0133845 A1 | 6/2007 | Fradkin et al. | |
| 2007/0173815 A1 | 7/2007 | Murase | |
| 2007/0219561 A1 | 9/2007 | Lavallee et al. | |
| 2008/0051779 A1 * | 2/2008 | Mackenzie | A61B 17/62 606/57 |
| 2008/0108912 A1 | 5/2008 | Node-Langlois | |
| 2008/0119719 A1 | 5/2008 | Ascenzi et al. | |
| 2008/0137923 A1 | 6/2008 | Spahn | |
| 2008/0177203 A1 | 7/2008 | von Jako | |
| 2008/0198966 A1 | 8/2008 | Hjarn et al. | |
| 2008/0234554 A1 * | 9/2008 | Vvedensky | A61B 17/62 600/300 |
| 2008/0243127 A1 | 10/2008 | Lang et al. | |
| 2008/0269741 A1 * | 10/2008 | Karidis | A61B 17/62 606/56 |
| 2008/0275467 A1 | 11/2008 | Liao et al. | |
| 2008/0319448 A1 * | 12/2008 | Lavallee | A61B 34/20 606/102 |
| 2009/0054887 A1 | 2/2009 | Podhajsky | |
| 2010/0036393 A1 | 2/2010 | Unsworth | |
| 2010/0087819 A1 * | 4/2010 | Mullaney | A61B 17/62 606/56 |
| 2010/0130858 A1 | 5/2010 | Arai et al. | |
| 2010/0286995 A1 | 11/2010 | Pekar et al. | |
| 2011/0004199 A1 | 1/2011 | Ross et al. | |
| 2011/0009868 A1 | 1/2011 | Sato | |
| 2011/0029116 A1 | 2/2011 | Jordan et al. | |
| 2011/0103556 A1 | 5/2011 | Carn | |
| 2011/0103676 A1 | 5/2011 | Mullaney | |
| 2011/0116041 A1 | 5/2011 | Hartung et al. | |
| 2011/0188726 A1 | 8/2011 | Nathaniel et al. | |
| 2011/0304332 A1 | 12/2011 | Mahfouz | |
| 2011/0313418 A1 * | 12/2011 | Nikonovas | A61B 17/62 606/56 |
| 2011/0313419 A1 * | 12/2011 | Mullaney | A61B 17/62 606/56 |
| 2011/0313424 A1 | 12/2011 | Bono et al. | |
| 2012/0071802 A1 | 3/2012 | Reiley et al. | |
| 2012/0130687 A1 | 5/2012 | Otto et al. | |
| 2012/0155732 A1 | 6/2012 | Finkelstein et al. | |
| 2012/0214121 A1 | 8/2012 | Greenberg | |
| 2012/0328174 A1 | 12/2012 | Jadiyappa | |
| 2012/0330312 A1 * | 12/2012 | Burgherr | A61B 17/62 606/54 |
| 2013/0018666 A1 * | 1/2013 | Murphy | G16H 20/40 705/2 |
| 2013/0089253 A1 * | 4/2013 | Chabanas | G06T 17/30 382/131 |

(56) References Cited

U.S. PATENT DOCUMENTS

| | | | |
|---|---|---|---|
| 2013/0096373 A1 | 4/2013 | Chabanas et al. | |
| 2013/0121612 A1 | 5/2013 | Falco, Jr. et al. | |
| 2013/0172783 A1 | 7/2013 | Ikits et al. | |
| 2013/0201212 A1* | 8/2013 | Haskell | G09G 5/00 345/632 |
| 2013/0211792 A1 | 8/2013 | Kang et al. | |
| 2013/0215114 A1* | 8/2013 | Cherkashin | A61B 6/584 345/420 |
| 2013/0253511 A1* | 9/2013 | Cheng | A61B 17/64 606/56 |
| 2013/0289575 A1* | 10/2013 | Edelhauser | A61B 17/7074 606/102 |
| 2014/0039663 A1 | 2/2014 | Boyer et al. | |
| 2014/0073907 A1 | 3/2014 | Kumar et al. | |
| 2014/0189508 A1 | 7/2014 | Granchi et al. | |
| 2014/0236153 A1* | 8/2014 | Edelhauser | A61B 17/62 606/56 |
| 2014/0270437 A1 | 9/2014 | Shreiber et al. | |
| 2014/0276821 A1* | 9/2014 | Murray | A61B 17/66 606/57 |
| 2014/0303486 A1 | 10/2014 | Baumgartner et al. | |
| 2014/0324403 A1 | 10/2014 | Gotte | |
| 2014/0328460 A1 | 11/2014 | Egli et al. | |
| 2014/0343586 A1 | 11/2014 | Sakuragi | |
| 2014/0350389 A1 | 11/2014 | Powell et al. | |
| 2014/0357984 A1 | 12/2014 | Wallace et al. | |
| 2014/0379356 A1 | 12/2014 | Sachdeva et al. | |
| 2015/0049083 A1 | 2/2015 | Bidne et al. | |
| 2015/0087965 A1 | 3/2015 | Tokuda et al. | |
| 2015/0227679 A1* | 8/2015 | Kamer | G16B 5/00 703/11 |
| 2015/0238271 A1 | 8/2015 | Wollowick et al. | |
| 2016/0042571 A1* | 2/2016 | Mikheev | G06T 19/20 345/419 |
| 2016/0045225 A1 | 2/2016 | Edelhauser et al. | |
| 2016/0092651 A1* | 3/2016 | Austin | G06Q 50/24 705/2 |
| 2016/0331463 A1* | 11/2016 | Notzli | G06T 19/20 |
| 2017/0281233 A1 | 10/2017 | Edelhauser et al. | |
| 2017/0303966 A1* | 10/2017 | Edelhauser | A61B 17/62 |
| 2017/0348054 A1* | 12/2017 | Kumar | A61B 34/10 |
| 2018/0055569 A1* | 3/2018 | Wahl | G06T 7/70 |
| 2018/0368928 A1* | 12/2018 | Abedinnasab | A61B 17/00234 |
| 2019/0282276 A1* | 9/2019 | Burgherr | G16H 50/50 |

FOREIGN PATENT DOCUMENTS

| | | |
|---|---|---|
| RU | 2448663 C1 | 4/2012 |
| RU | 2471447 C1 | 1/2013 |
| RU | 2489106 C2 | 8/2013 |
| WO | 2009076296 A2 | 6/2009 |
| WO | 2010104567 A1 | 9/2010 |
| WO | 2013013170 A1 | 1/2013 |

OTHER PUBLICATIONS

European Patent Office (ISA), International Search Report and Written Opinion dated Jun. 25, 2013 for International Application No. PCT/US2013/024548,International filing date Feb. 3, 2013.

Extended European Seach Report for Application No. 14154820.6 dated Jun. 16, 2014.

Extended European Search Report for Application No. EP17173905, dated Oct. 30, 2017.

IMED Surgical, Adam Frame with Paley's Method, Workshop, Oct. 2010.

LITOS GmbH, "Ilizarov Hexapod System," available from http://d3llyibkg2zj6z.cloudfront.net/ImagemAnexo/Ilozarov-Hexapod-System.- PDF, dated May 23, 2007.

Response Ortho LLC, Smart Correction Computer Assisted Circular Hexapod System Brochure, date not known.

Smart Correction, Computer-Assisted Circular External Fixator System, website printout, Feb. 2, 2011.

Vreden Russian Research Institute of Traumatology and Orthopedics Ortho-SUV Ltd., Deformity Correction and Fracture Treatment by Software-based Ortho-SUV Frame, Saint-Petersburg, 2013.

* cited by examiner

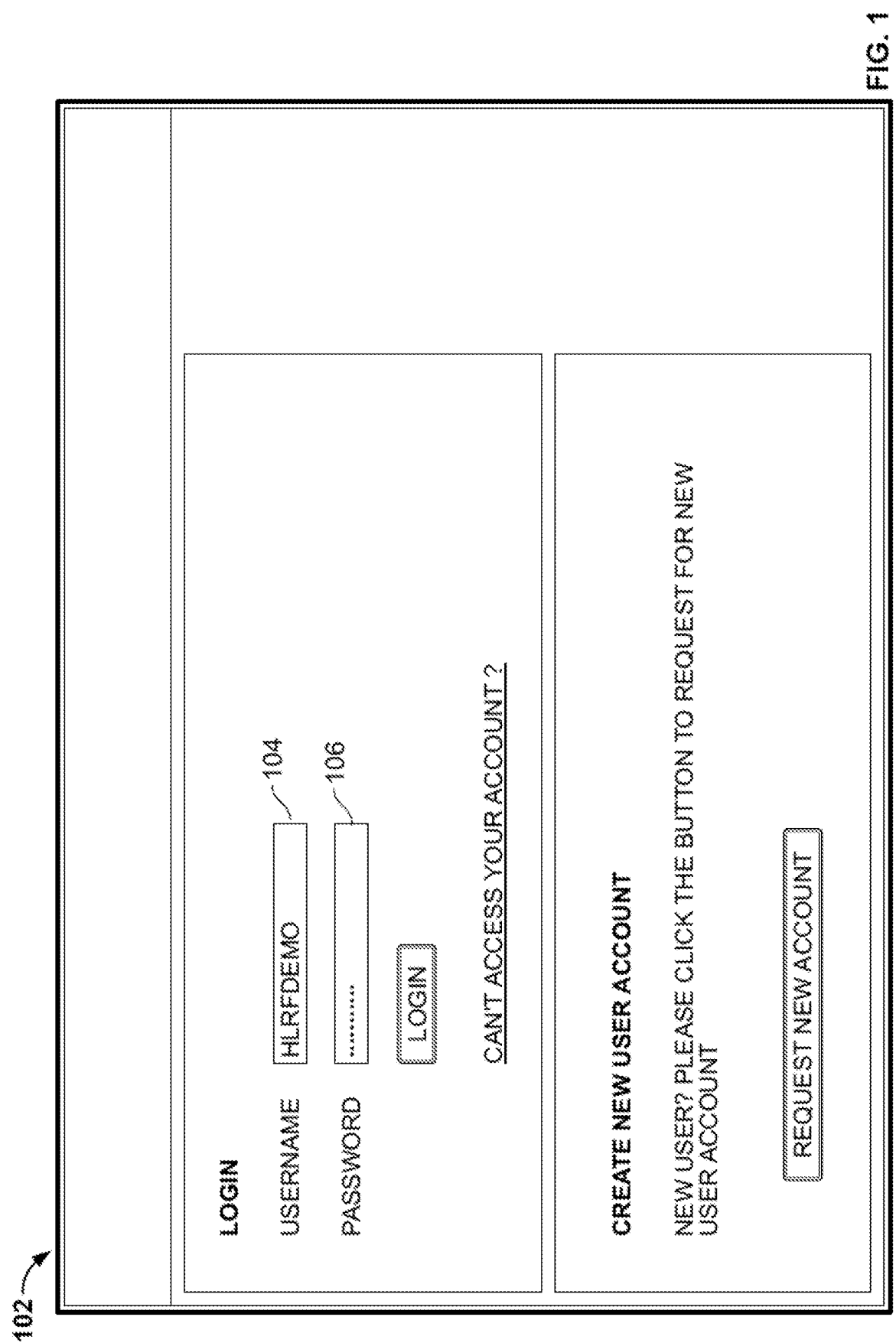

FIG. 2

HOME

START NEW CASE — 112

EXPRESS SEARCH

SHOW CASES CREATED: [IN LAST 30 DAYS ▼]   ENTER CASE ID: [        ]   [SEARCH]   ENTER KEYWORD: [        ]   [SEARCH]

[ADVANCED SEARCH OPTIONS]

⦿ MY CASES
◯ CASES FROM OTHERS

| CASE ID | PATIENT NAME | ANATOMY | CREATION DATE | MODIFIED DATE | | | |
|---|---|---|---|---|---|---|---|
| CS0000001 | JOHN A | LEFT FEMUR | MM/DD/YYYY 10:16:40 PM | MM/DD/YYYY 9:34:30 PM | OPEN | DELETE | SHARE |
| CS0000002 | JOHN B | LEFT FEMUR | MM/DD/YYYY 10:11:00 PM | MM/DD/YYYY 10:13:30 PM | OPEN | DELETE | SHARE |
| CS0000003 | JOHN C | LEFT FEMUR | MM/DD/YYYY 10:12:10 PM | MM/DD/YYYY 10:13:11 PM | OPEN | DELETE | SHARE |
| CS0000004 | JOHN D | LEFT FEMUR | MM/DD/YYYY 10:08:15 PM | MM/DD/YYYY 10:09:14 PM | OPEN | DELETE | SHARE |
| CS0000005 | JOHN E | LEFT FEMUR | MM/DD/YYYY 9:57:51 PM | MM/DD/YYYY 10:08:02 PM | OPEN | DELETE | SHARE |
| CS0000006 | JOHN F | LEFT FEMUR | MM/DD/YYYY 8:43:11 PM | MM/DD/YYYY 9:57:25 PM | OPEN | DELETE | SHARE |
| CS0000007 | JOHN G | LEFT FEMUR | MM/DD/YYYY 8:47:24 PM | MM/DD/YYYY 8:48:18 PM | OPEN | DELETE | SHARE |
| CS0000008 | JOHN H | LEFT FEMUR | MM/DD/YYYY 8:41:53 PM | MM/DD/YYYY 8:42:03 PM | OPEN | DELETE | SHARE |
| CS0000009 | JOHN I | LEFT FEMUR | MM/DD/YYYY 8:40:41 PM | MM/DD/YYYY 8:40:51 PM | OPEN | DELETE | SHARE |
| CS0000010 | JOHN J | LEFT FEMUR | MM/DD/YYYY 8:39:41 PM | MM/DD/YYYY 8:39:50 PM | OPEN | DELETE | SHARE |

NEXT >

WELCOME USER  SETTINGS | HELP | LOGOUT 110, 114

HOME
CASE DETAILS | DEFORMITY DEFINITION | RING CONFIGURATION | STRUT CONFIGURATION | LAF INPUT | CORRECTION PLAN | STUDY REPORT

WELCOME USER SETTINGS | HELP | LOGOUT
SMART TOOL

CS0000001

START DATE [MM/DD/YYYY] 📅

[GENERATE CORRECTION SCHEDULE]

0000000000

[RUN SIMULATION]

[SAVE CASE DATA]    [<< PREVIOUS]  [NEXT >>]

| DAY | DATE | STRUT1 (DEG) | | STRUT2 (DEG) | | STRUT3 (DEG) | |
|---|---|---|---|---|---|---|---|
| | | POSITION | ANGLE | POSITION | ANGLE | POSITION | ANGLE |
| 1 | MM/DD/YYYY | 277.2 | 26.4 | 18.4 | 43.6 | 178.9 | 12.2 |
| 2 | MM/DD/YYYY | 279.2 | 26.9 | 16 | 42.5 | 178.5 | 13.6 |
| 3 | MM/DD/YYYY | 281.2 | 27.4 | 14.1 | 41.3 | 178.2 | 14.9 |
| 4 | MM/DD/YYYY | 283.3 | 27.8 | 12.5 | 40 | 177.8 | 16.3 |
| 5 | MM/DD/YYYY | 285.5 | 28.2 | 11.1 | 38.6 | 177.4 | 17.7 |
| 6 | MM/DD/YYYY | 287.7 | 28.6 | 10 | 37.2 | 177 | 19.1 |
| 7 | MM/DD/YYYY | 289.9 | 28.9 | 9.1 | 35.8 | 176.7 | 20.5 |

FIG. 14

HOME

WELCOME USER SETTINGS | HELP | LOGOUT

CASE DETAILS  DEFORMITY DEFINITION  RING CONFIGURATION  STRUT CONFIGURATION  LAF INPUT  CORRECTION PLAN  STUDY REPORT  SMART TOOL

[ PRINT REPORT ]

STUDY REPORT

CASE DETAILS

| CASE ID | CS0000001 | CREATED DATE | MM/DD/YYYY |
|---|---|---|---|
| PATIENT NAME | JOHN A | DATE OF BIRTH | MM/DD/YYYY |
| SEX | MALE | ANATOMY | LEFT TIBIA |

DEFORMITY DEFINITION

| | AP | LATERAL | AXIAL |
|---|---|---|---|
| TRANSLATION(MM) | 0 MM - MEDIAL | 0 MM - ANTERIOR | 23.9 MM - LONG |
| ANGULATION(DEG) | 13 DEG - APEXLATERAL | 15.6 DEG - APEXPOSTERIOR | 4.5 DEG - EXTERNAL |

LAF INPUT

| | AP OFFSET (MM) | LATERAL OFFSET (MM) | AXIAL OFFSET (MM) |
|---|---|---|---|
| LAF POSITIN | 0 | 0 | 0 |

[ SAVE CASE DATA ]

[ << PREVIOUS ]  [ NEXT >> ]

HOME

CS0000001
ANATOMY                FEMUR                    CREATED DATE         MM/DD/YYYY
PATIENT DETAILS
PATIENT NAME           JOHN A                   DATE OF BIRTH        MM/DD/YYYY
SEX                    MALE
STUDIES            CREATE NEW               CASE SUMMARY

| S NO | STUDY DATE | STUDY NOTES       |      |        |
|------|------------|-------------------|------|--------|
| 1    | MM/DD/YYYY | ENTER NOTES HERE  | OPEN | DELETE |

WELCOME USER  SETTINGS | HELP | LOGOUT

SOFTWARE FOR USE WITH DEFORMITY CORRECTION

CROSS-REFERENCE TO RELATED APPLICATIONS

This application is a continuation of U.S. patent application Ser. No. 15/627,900, filed Jun. 20, 2017, which is a continuation of U.S. Pat. No. 9,724,129, filed Oct. 29, 2015, which is a continuation of U.S. Pat. No. 9,204,937, filed on Feb. 19, 2013, the disclosures of which are incorporated by reference herein.

FIELD OF THE INVENTION

The present disclosure relates to software used in planning the correction of bone deformities preoperatively or postoperatively, and in particular relates to virtually manipulating rings and struts of an external fixation frame in order to plan the steps for making a desired correction to two or more bone portions of a patient.

BACKGROUND OF THE INVENTION

Currently, external fixation systems may be used to correct skeletal deformities using the distraction osteogenesis process, for example. The Ilizarov external fixation device (or similar system) may be used for such a purpose. The Ilizarov-type devices generally translate bone segments by manipulating the position of rings connected to each bone segment.

These external fixation devices generally utilize threaded rods fixated to through-holes in the rings to build the frame. In order to build the desired frame, these rods generally have to have different lengths.

Once the frame is installed, the patient or surgeon moves the rings or percutaneous fixation components manually or mechanically by adjusting a series of nuts.

As fixation devices become more complex, the task of determining the optimal lengths and positions of the struts with respect to rings of the fixation frame, as well as creating a correction plan for manipulating the struts to correct the bone deformity, becomes more difficult.

The increasing difficulty of these determinations decreases the attractiveness of using complex fixation frames. It would be advantageous to have an at least partially automated method for determining the optimal configuration of a fixation frame in reference to a deformed bone, as well as a correction plan for manipulating the fixation frame to correct the bone deformity.

BRIEF SUMMARY OF THE INVENTION

In one embodiment of the invention, a method of generating a correction plan for correcting a deformed bone includes displaying on a visual medium a first model of the deformed bone in a first plane, the first model of the deformed bone having a position and orientation on the visual medium. A model bone having a first configuration is overlaid on the first model of the deformed bone in the first plane and a position and orientation of the model bone is manipulated into a second configuration being substantially similar to the position and orientation of the first model of the deformed bone in the first plane. A second model of the deformed bone is displayed on the visual medium in a second plane, the second model of the deformed bone having a position and orientation on the visual medium. The model bone in the second configuration is overlaid on the second model of the deformed bone in the second plane and the position and orientation of the model bone is manipulated into a third configuration being substantially similar to the position and orientation of the second model of the deformed bone in the second plane. The model bone in the third configuration is projected onto a three dimensional axis. A model of first and second fixation rings is and positional data corresponding to a position and orientation of the models of the first and second fixation rings with respect to the three dimensional axis is displayed. The positional data corresponding to the models of the first and second fixation rings is manipulated until the first and second model fixation rings are each in a desired position relative to the model bone in the third configuration.

The first model of the deformed bone may be an x-ray image displayed on the visual medium in an anterior-posterior view, while the second model of the deformed bone may be an x-ray image displayed on the visual medium in a lateral view.

Positional data corresponding to the position and orientation of the model bone with respect to the three dimensional axis may be displayed on the visual medium. The model bone may have a plurality of portions and the positional data corresponding to the model bone may include coordinate locations and angular orientations of at least one of the plurality of portions of the model bone on the three dimensional axis. The step of manipulating the position and orientation of the model bone may include one of entering numerical values into an input box and moving a slide-bar corresponding to the numerical values.

The step of manipulating the position and orientation of the model bone may include changing the position and orientation of the model bone in an anterior-posterior plane, a lateral plane, and an axial plane. Changing the position and orientation of the model bone in the anterior-posterior plane, the lateral plane, and the axial plane may each include changing at least one of a translation or angulation value.

Combinations of sizes of a plurality of model struts to connect the models of the first and second fixation rings may be determined with an algorithm using the positional data corresponding to the desired position of the models of the first and second fixation rings. One of the combinations of sizes of the plurality of model struts may be selected. The correction plan may be determined with an algorithm using the manipulated position and orientation of the model bone in the third configuration, the positional data corresponding to the desired position of the models of the first and second fixation rings, and the selected combinations of sizes of the plurality of model struts. The correction plan describes length adjustments that should be made to the plurality of model struts over a period of time. The correction plan results in length adjustments made to the plurality of model struts such that the models of the first and second fixation rings are in corrected positions.

In another embodiment of the invention, a method of generating a correction plan for correcting a deformed bone includes the step of displaying on a visual medium a first model of the deformed bone in a first plane, the first model of the deformed bone having a position and orientation on the visual medium. A model bone having a first configuration is overlaid on the first model of the deformed bone in the first plane and a position and orientation of the model bone is manipulated into a second configuration being substantially similar to the position and orientation of the first model of the deformed bone in the first plane. A second model of the deformed bone is displayed on the visual medium in a second plane, the second model of the deformed bone having a position and orientation on the visual medium. The model bone in the second configuration is overlaid on the second model of the deformed bone in the second plane and the position and orientation of the model bone is manipulated into a third configuration being substantially similar to the position and orientation of the second model of the deformed bone in the second plane. The model bone is projected in the third configuration onto a three dimensional axis. A model of a first fixation ring having a first configuration and positional data corresponding to a position and orientation of the model of the first fixation ring with respect to the three dimensional axis is displayed. The positional data corresponding to the position and orientation of the model of the first fixation ring is manipulated into a second configuration relative to the model bone being substantially similar to a position and orientation of a first fixation ring relative to the deformed bone.

The first model of the deformed bone may be an x-ray image displayed on the visual medium in an anterior-posterior view, and the second model of the deformed bone may be an x-ray image displayed on the visual medium in a lateral view.

Positional data corresponding to the position and orientation of the model bone with respect to the three dimensional axis is displayed on the visual medium. The model bone has a plurality of portions and the positional data corresponding to the model bone includes coordinate locations and angular orientations of at least one of the plurality of portions of the model bone on the three dimensional axis.

The step of manipulating the position and orientation of the model bone includes one of entering numerical values into an input box and moving a slide-bar corresponding to the numerical values. The step of manipulating the position and orientation of the model bone includes changing the position and orientation of the model bone in an anterior-posterior plane, a lateral plane, and an axial plane. Changing the position and orientation of the model bone in the anterior-posterior plane, the lateral plane, and the axial plane each includes changing at least one of a translation or angulation value.

A plurality of model struts having a first configuration and positional data corresponding to a position and orientation of the plurality of model struts in relation to the model of the first fixation ring are displayed on the visual medium. The positional data corresponding to the position and orientation of the plurality of model struts is manipulated into a second configuration relative to the model of the first fixation ring being substantially similar to a position and orientation of a plurality of struts relative to the first fixation ring. A position and orientation of a second model fixation ring is determined, wherein the positional data of the second model fixation ring relative to the model bone is substantially similar to a position and orientation of a second fixation ring relative to the deformed bone.

The correction plan is determined with an algorithm using the manipulated position and orientation of the model bone in the third configuration, the manipulated positional data corresponding to the first model fixation ring, and the manipulated positional data corresponding to the plurality of model struts. The correction plan describes length adjustments that should be made to the plurality of model struts over a period of time.

BRIEF DESCRIPTION OF THE DRAWINGS

FIG. 1 illustrates a login screen of a deformity correction application.

FIG. 2 illustrates a home page screen of a deformity correction application.

FIG. 3 illustrates a case details screen of a deformity correction application.

FIG. 6 illustrates an alternate deformity definition function of a deformity correction application.

FIG. 9 illustrates a first strut configuration screen of a pre-operative mode of a deformity correction application.

FIG. 10 illustrates a second strut configuration screen of a pre-operative mode of a deformity correction application.

FIG. 11 illustrates a limiting anatomical factor input screen of a deformity correction application.

FIG. 12 illustrates a correction plan generation screen of a deformity correction application during the generation of a correction plan.

FIG. 13 illustrates a correction plan generation screen of a deformity correction application displaying the correction plan.

FIG. 14 illustrates a study report screen of a deformity correction application.

FIG. 15 illustrates a smart tool screen of a deformity correction application.

FIG. 16 illustrates a second ring configuration screen of a post-operative mode of a deformity correction application.

FIG. 18 illustrates an existing case screen of a deformity correction application.

DETAILED DESCRIPTION

Figure 4:
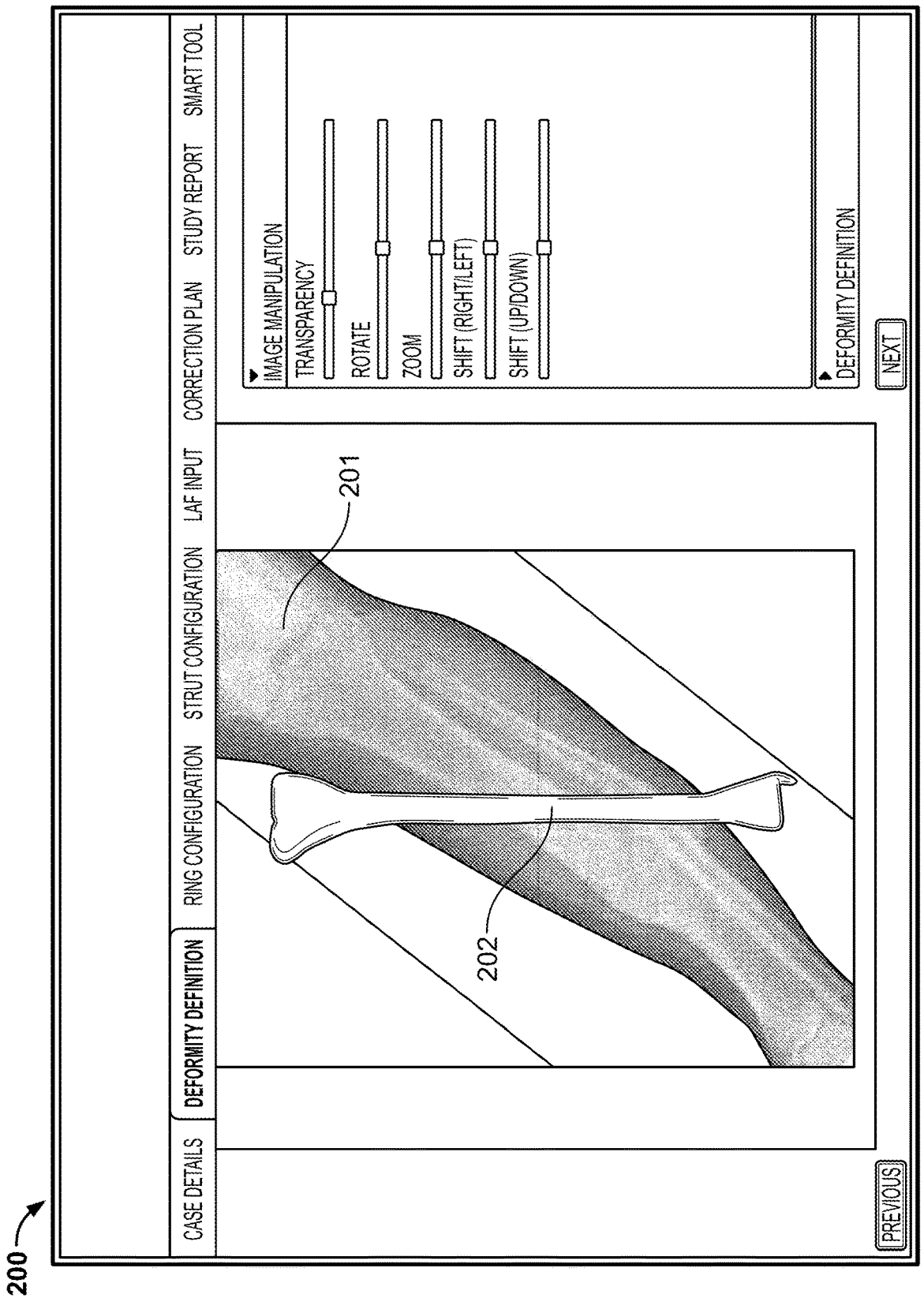
FIG. 4 illustrates an image manipulation function of a deformity correction application.

In one embodiment of the invention, software aids a user, such as a physician, surgeon, or other medical personnel, in planning and carrying out the correction of a bone deformity using a limb reconstruction frame using a web application, for example.

As shown in FIG. 1, upon starting the application, the user is presented with a login screen 102. The login screen 102 preferably includes a username field 104 and password field 106 in which the user enters, respectively, a username and password to gain further access to the application. This step of authentication may, for example, help maintain compliance with patient privacy regulations. In cases where a first time user tries to gain further access to the application, a new user account will have to be created.

As shown in FIG. 2, upon logging in, the user is taken to the home page 110 (FIG. 2). From the home page 110, the user has the option of starting a new case by choosing the new case option 112, or choosing an existing case by, for example, searching for an existing case using keywords or case number identifiers or choosing from a list of existing cases 114. Each listed case includes summary information of the case, such as case numbers, patient names, relevant anatomy to be corrected, and dates that the case was created and/or last modified. The initial list of displayed existing cases 114 can, for example, display the most recent cases viewed by the user. For existing cases, the user also has the option to share the case with another user. For example, a physician can choose the case sharing option to send the case information to another physician using the software. This might be useful, for example, if the first physician wants advice from a second physician on the case, or if the first physician believes his case will be helpful to a second physician handling a similar case.

Figure 3:
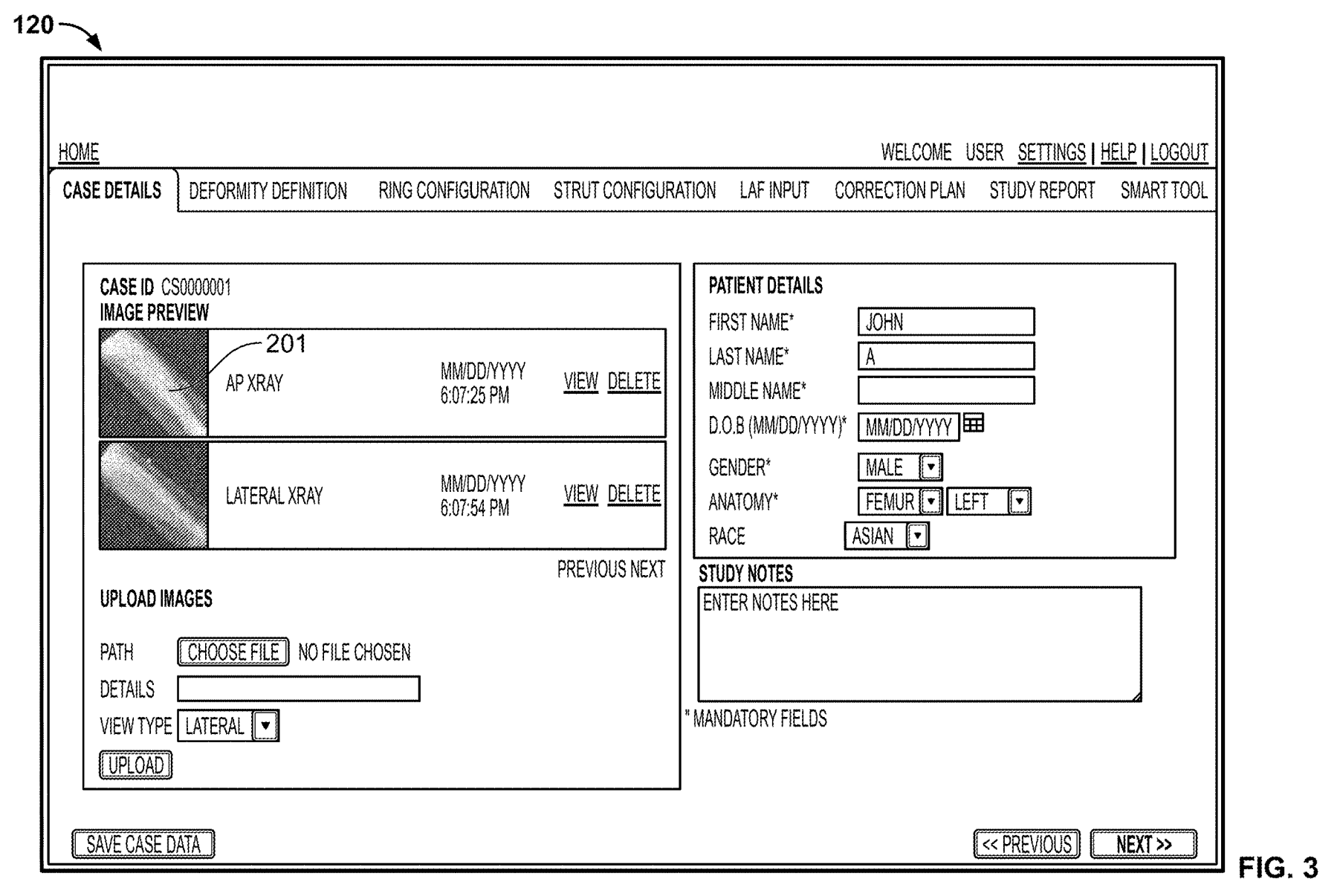

A user chooses the new case option for a patient whose information has not yet been entered into the software. When a user selects the new case option 112, the user is brought to a case details screen 120 (FIG. 3). At the case details screen 120, the user has the option of entering, viewing, or modifying patient details such as the patient's name, gender, race, date of birth, anatomy relevant to the case, and notes as the user sees fit. The user is presented with a preview of uploaded X-ray images 201 if any have been uploaded. If no X-ray images 201 have been uploaded, the user can upload images, for example one X-ray image of the deformed bone in the anterior-posterior ("AP") plane and one X-ray image of the deformed bone in the lateral plane. These X-ray images 201, if used, may help the user to define the bone deformity, described more fully below. To upload an X-ray image 201, the user chooses the "choose file" option and is able to import the desired image file from a memory device, such as a flash drive. Prior to uploading, the user also provides details relating to the image 201, such as the view (e.g. lateral plane) in which the image was taken. Upon selecting the anatomy within the patient details (e.g. right or left side, femur, tibia, humerus, radius), the user can proceed to define the deformity.

A deformity definition screen 200 (FIGS. 4-5) within the application presents a model bone 202. The deformity definition screen 200 includes an image manipulation function and a deformity definition function. In the image manipulation function, shown in FIG. 4, the application presents a model bone 202 overlaid on an X-ray image 201 previously uploaded on the case details screen 120. The model bone 202 is chosen based on input of the relevant anatomy (e.g. left femur) from the case details screen 120, and is initially presented in a non-deformed state. The model bone 202 is presented in the same plane which the user defined for the X-ray image 201. The image manipulation function allows the user to manipulate the X-ray image 201, for example by rotating, zooming, or repositioning the image. The user can also manipulate the transparency of the X-ray image 201 as desired for the best view of the model bone 202 in relation to the X-ray image. The user manipulates the X-ray image 201 with the goal of generally matching the size and position of the bone shown in the X-ray image with the model bone 202 displayed on the deformity definition screen 200. The image 201 will often require manipulation because X-ray images, along with the actual bones being imaged, may vary in size and the initial position of the uploaded image may not align with the position of the model bone 202. Once the user is satisfied that the model bone 202 generally corresponds to the size and position of the X-ray image 201, the user can choose to begin the deformity definition function. This step can be repeated for each X-ray image 201. For example, if a user uploads one X-ray image 201 in each of the AP and lateral planes, two separate image manipulations could be performed.

Figure 5:
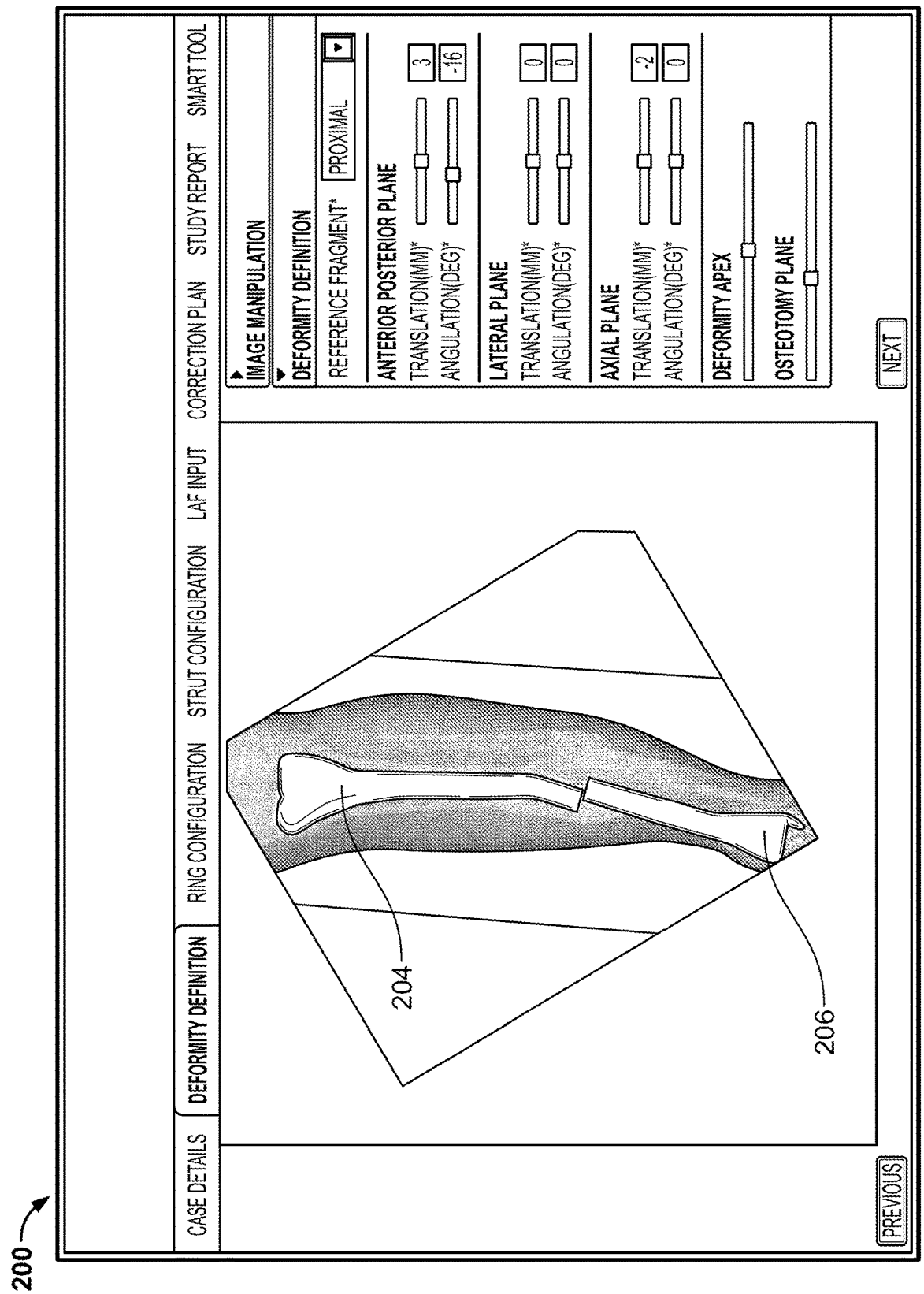
FIG. 5 illustrates a deformity definition function of a deformity correction application.

The deformity definition function of the deformity definition screen 200 is illustrated in FIG. 5. The manipulated X-ray image 201 is displayed in the background with the model bone 202 in the foreground. The model bone 202 includes a plurality of portions, including a proximal portion 204 and a distal portion 206. A panel, to the right of the model bone 202 as illustrated in FIG. 5, allows the user to enter parameters relating to geometry of the deformed bone to modify the bone model 202 to approximate the actual bone deformity.

To start, the user designates a reference bone fragment, for example either the proximal portion 204 or distal portion 206. The reference fragment, as depicted in FIG. 5, remains aligned with the vertical axis during manipulation of the bone model 202, with the non-reference fragment changing position, with respect to the reference fragment, based on user input. The user inputs values for translation and angulation of the non-reference fragment with respect to the reference fragment in one or more of the AP plane, the lateral plane, and the axial plane. The user can input this data by, for example, entering the numerical value of translation (for example in millimeters) and/or angulation (for example in degrees) of the non-reference fragment with respect to the reference fragment in any of the desired planes. The user may alternately or additionally change the translation and/or angulation values using a slide-bar function in which sliding a bar in one direction decreases the value of the relevant parameter while sliding the bar in the other direction increases the value.

The user can also input a value for the deformity apex and the position of the osteotomy along the length of the model bone 202. In FIG. 5, the deformity apex would be the point at which a line through the center of the proximal portion 204 intersects with the distal portion 206. A change to the deformity apex value would be visualized in FIG. 5 as a change in the location at which the angled deformity of the proximal portion 204 is seen. The osteotomy plane, as seen in FIG. 5, is the location of the separation between the proximal portion 204 and the distal portion 206.

As the user enters or changes the above-mentioned values, the graphical representation of the non-reference bone portion will change to reflect the new values. The change in the position of the model bone 202 against the backdrop of the X-ray image 201 allows the user to obtain visual confirmation that the parameters applied to the model bone accurately represent the parameters of the deformed bone. This step may be performed using more than one X-ray image 201, or without any X-ray images, as described below. When using multiple X-ray images 201, each can be viewed while setting values for the deformity. For example, a user may view the model bone 202 against an X-ray image 201 in the AP plane while setting values for the deformity in the AP plane, and then switch to a view of the model bone 202 against an X-ray image 201 in the lateral plane while setting values for the deformity in the lateral plane.

Figure 6:
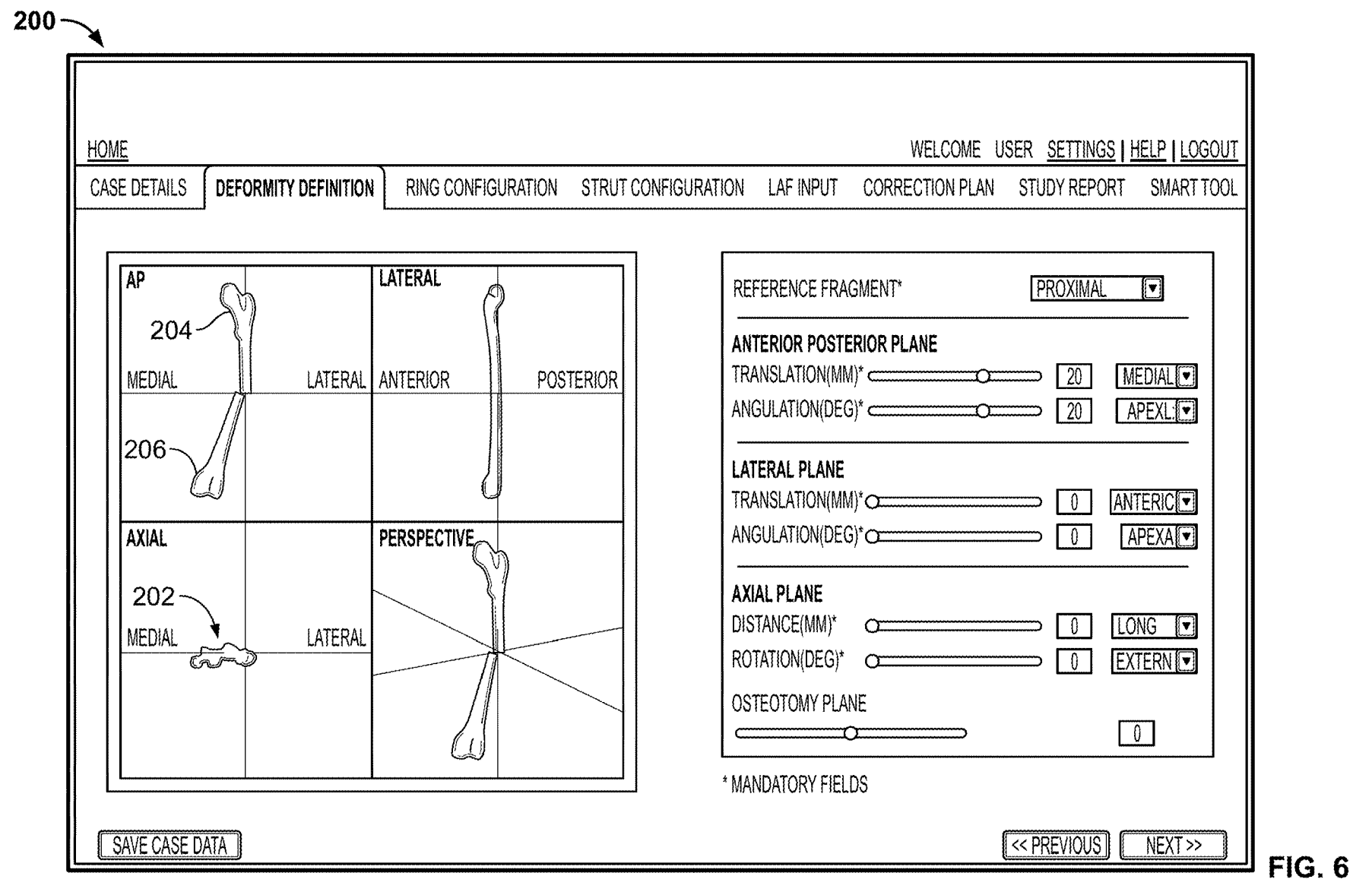

X-ray images 201 are not a necessary part of the deformity definition step. For example, in addition or as an alternative to using X-ray images 201, the user can perform the same model bone 202 manipulations without the backdrop of an X-ray image. As seen in FIG. 6, a deformity definition screen 200 presents a model bone 202 simultaneously in the AP, lateral, and axial planes, as well as a perspective view. One or more combinations of views, including additional views not specifically identified herein, may be used and is largely a matter of design choice. Similar to the process described with reference to FIG. 5, the user enters values corresponding to the position and orientation of the non-reference fragment (distal portion 206 as illustrated in FIG. 6) in the AP plane, the lateral plane, and the axial plane. The use may also enter or change a value for the osteotomy plane and the deformity apex (deformity apex option not illustrated in FIG. 6), largely in the same manner as described with reference to FIG. 5.

For each value entered, the user can select a corresponding direction from a drop down menu. For example, the user can enter a 20 mm translation in the AP plane, and assign that value either a medial or lateral direction. Alternatively, the value can be a positive or negative value, with one direction assigned to positive values and the opposite direction assigned to negative values (e.g. 20 mm corresponding to a 20 mm medial translation and—20 mm corresponding to a 20 mm lateral translation). Similar to the method described with reference to FIG. 5, the user can directly enter numerical values based on experience or previous measurements of the bone deformity. In addition or as an alternative, the user can change the position of the slide bars corresponding to the non-reference bone parameters to reach a final value that accurately represents the geometry of the bone deformity.

Figure 7:
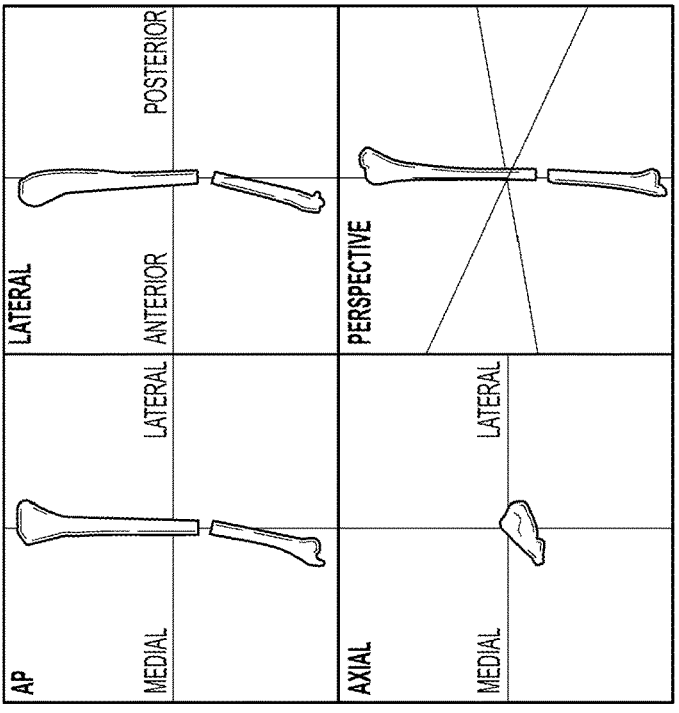
FIG. 7 illustrates a first ring configuration screen of a deformity correction application.

Once the user is satisfied that the model bone 202 is an accurate representation of the deformed bone, the user can proceed to the first ring configuration screen 250 (FIG. 7). The first ring configuration screen 250 allows the user to choose to continue in either a pre-operative ("pre-op") or post-operative ("post-op") mode by selecting the respective radio button. Generally speaking, the pre-op mode is used prior to the surgical fixation of the limb reconstruction device to the deformed bone. The post-op mode is to be used after the limb reconstruction device, with associated rings and struts, has already been affixed to the patient. In a single case, the pre-op mode can be used alone, the post-op mode can be used alone, or each mode can be used prior to and following surgery, respectively.

Figure 8:
FIG. 8 illustrates a second ring configuration screen of a pre-operative mode of a deformity correction application.

If the pre-op mode is selected, the user can continue to a pre-op ring configuration screen 300 (FIG. 8). At this point, the user inputs the size of the desired rings, including a reference ring 305 and a moving ring 310. For example, a user may be able to choose between a 155 mm, 180 mm, or 210 mm ring. The user may also be able to choose the type of ring, such as a full ring or partial ring. Different types of rings are known in the art and the inclusion of different rings as options in the software is largely a matter of design choice.

The rings 305, 310 are displayed along with the model bone 202 on the screen, preferably in an AP view, a lateral view, and an axial view. Additional views, such as a perspective view, may be included. The position and orientation of the proximal portion 204 and distal portion 206 of the model bone 202 are based on the input received during the deformity definition stage.

Once a size and/or type of ring is selected for the reference ring, it is displayed perpendicular to the reference fragment with a longitudinal axis of the reference fragment extending through the center of the reference ring. Similarly, once a size and/or type of ring is selected for the moving ring, it is displayed perpendicular to the non-reference fragment with a longitudinal axis of the non-reference fragment extending through the center of the moving ring. Similar to the deformity definition screen 200, the user enters position and orientation values for the reference ring 305 and the moving ring 310. For the rings, the user can directly enter the values, or move a slide-bar corresponding to the values to scroll through a range of values. Because this is the pre-op mode and no fixation device has yet been attached to the patient, the user chooses the ring sizes, positions and orientations that he believes will be effective for the correction based, for example, on his experience and knowledge.

As the values are entered, or as the slide-bar is moved, the graphical representation of the rings changes to reflect the new values. For the reference ring 305, the position values include an AP offset, a lateral offset, an axial offset, and an axial angle. The moving ring 310 includes these values, and additionally includes an AP angle and a lateral angle. Once the user is satisfied that the reference ring 305 and moving ring 310 are at locations on the model bone 202 representative of where the actual rings should be located on the patient's deformed bone, the user can proceed to the first strut configuration screen 350. The software may also provide maximum and minimum values for the placement and orientation of the reference ring 305 and moving ring 310, based, for example, on the feasibility of actually achieving those values in the operating room. These limits would help ensure that the planned values for the ring positions input by the user can likely be achieved during surgery on the patient.

Figure 9:
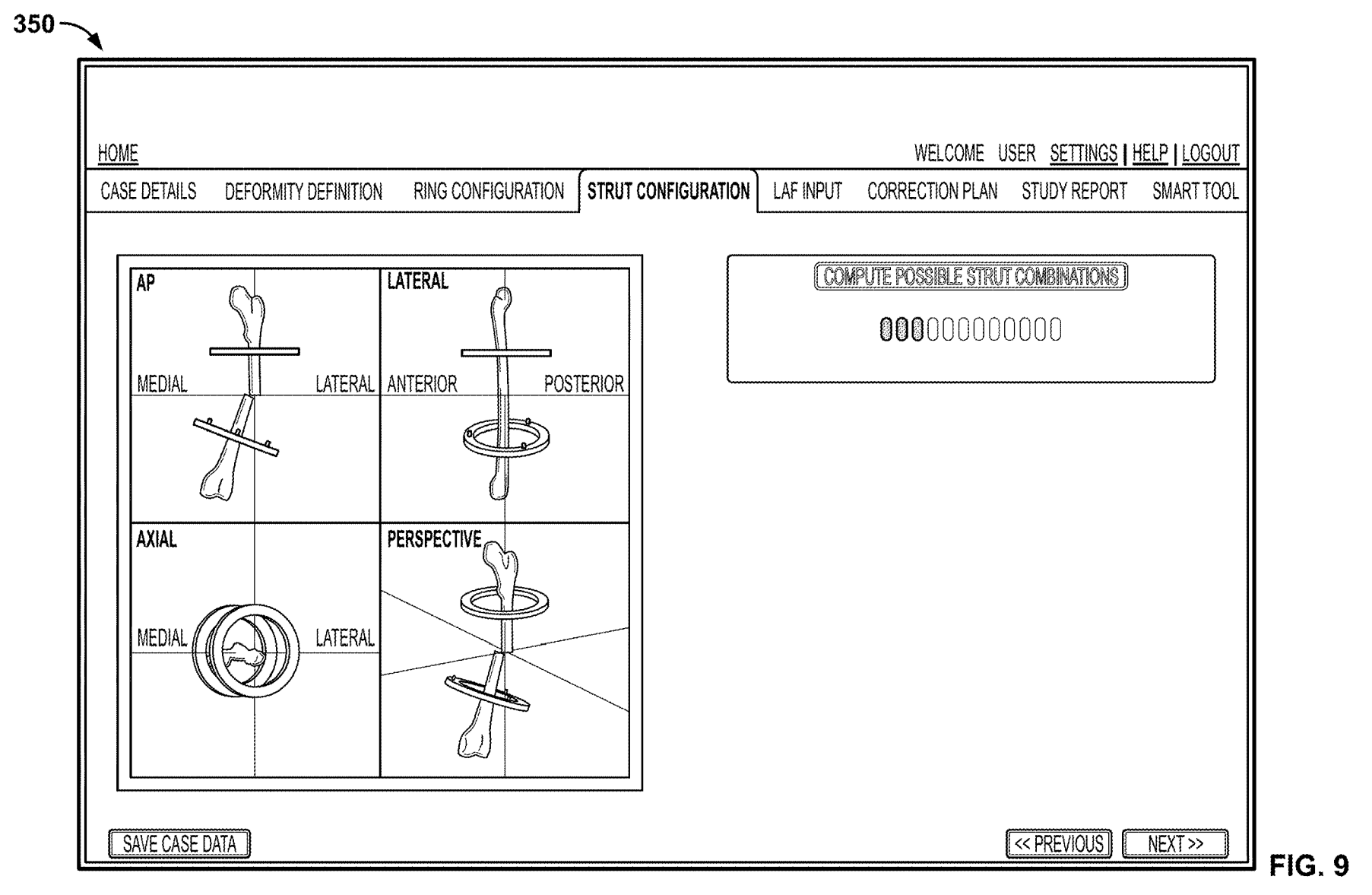
Figure 10:
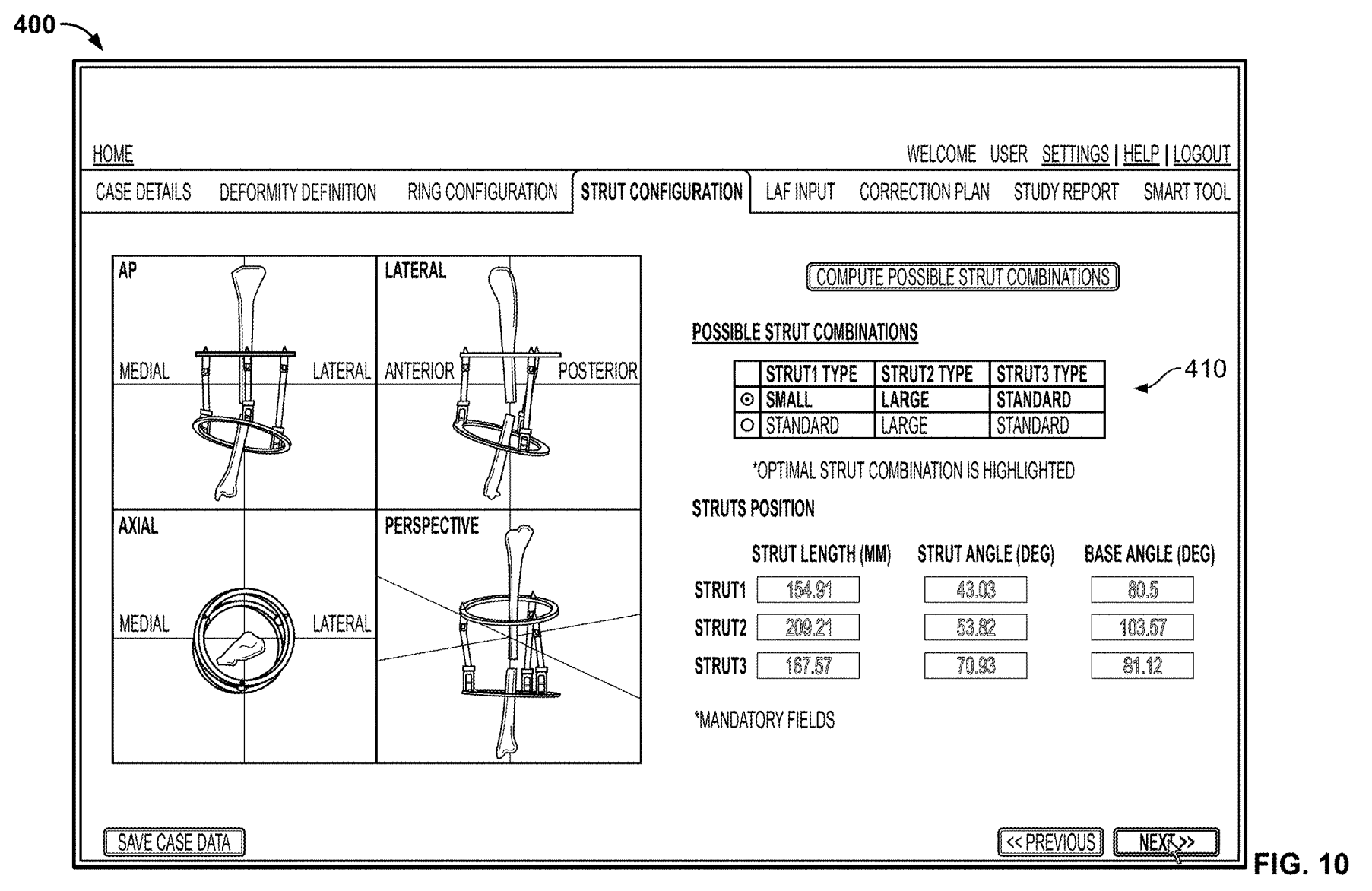

The first strut configuration screen 350 allows the user to initiate an automatic calculation of possible strut combinations to connect the reference ring 305 to the moving ring 310 (FIG. 9). Once the calculation is complete, the user is presented with the second strut configuration screen 400 that displays at least one possible strut combination, and preferably more than one (FIG. 10). The possible strut combinations 410 are presented in a table with a description of each strut in a particular combination. The model bone 202 and rings 305, 310 are displayed in an AP view, a lateral view and an axial view. Additional views such as a perspective view can be included. This display is based on values entered during the deformity definition and ring configuration steps. Additionally, the struts of a particular strut combination 410 are displayed with the model bone and rings. Each strut combination 410 includes a radio button.

When the user selects a particular strut combination 410 by selecting the corresponding radio button, the views update to show that particular strut combination. An optimal strut combination is highlighted among all the strut combinations 410 to suggest to the user a particularly desired combination to select. Among other factors, the optimal strut combination is based on the combination that will require the least amount of strut change-outs during the correction procedure.

In the pre-op mode, when a particular strut combination 410 is selected, the orientation of each strut, including strut length, strut angle, and base angle are displayed. After selecting a desired strut combination 410, the user may optionally choose to over-constrain the frame with an additional strut (not illustrated). For example, in a fixation frame that uses three struts, a fourth strut could be added after the three-strut combination is chosen. The fourth strut over-constrains the fixation frame by increasing stiffness and reducing play in the frame. The length, angle, and position of the additional strut is provided by the software once the option for the additional strut is chosen. Once the desired strut combination is chosen, and any additional desired struts are chosen, the user proceeds to a limiting anatomical factor ("LAF") input screen 450.

Figure 11:
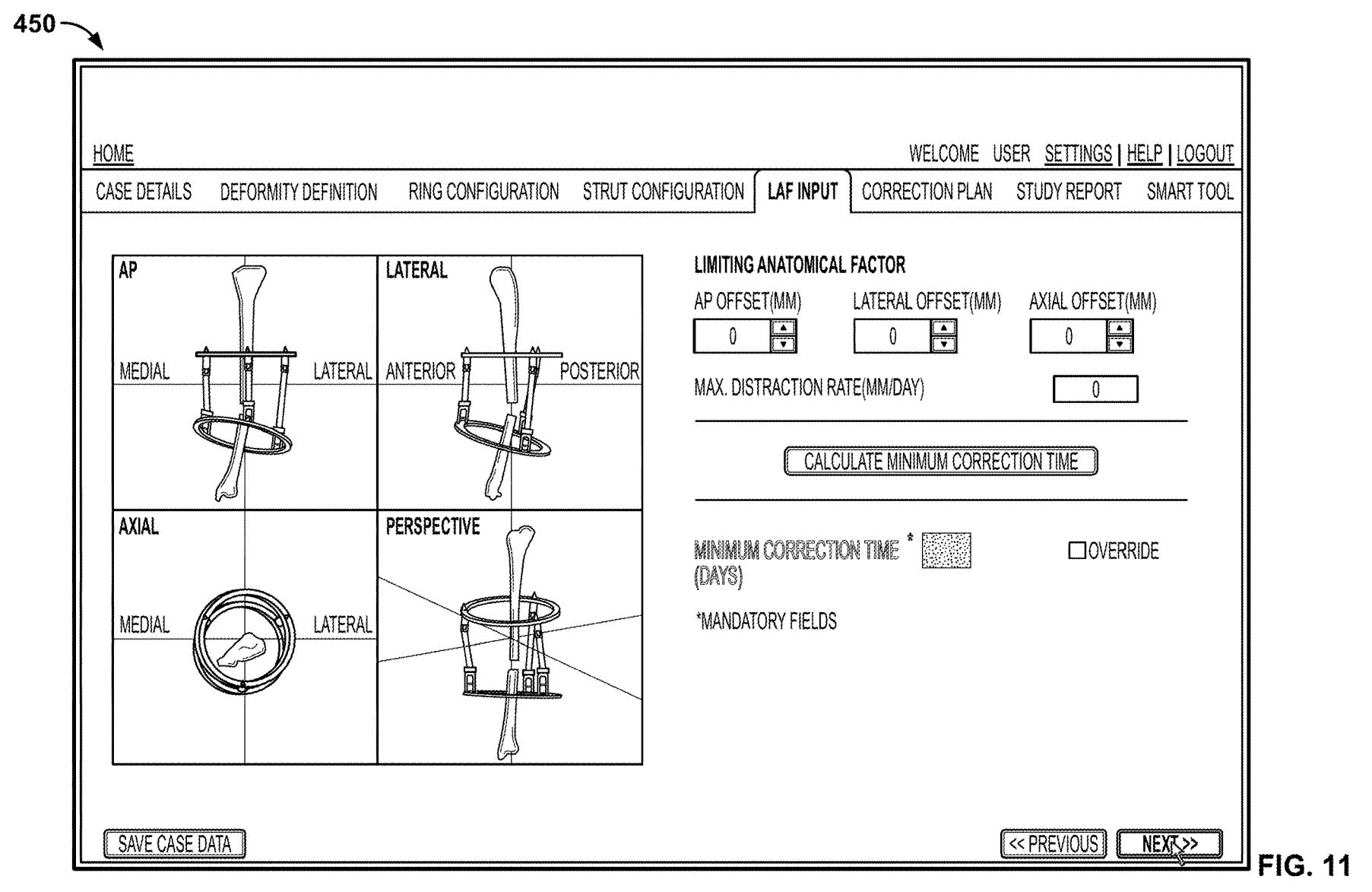

The LAF input screen 450 (FIG. 11) allows a user to input a limiting anatomical factor ("LAF") and to calculate a minimum amount of time for the correction process. The LAF is a reference point to which a user may want to set a maximum distraction rate or velocity. For example, if a segment of bone is to be moved a certain distance per day, surrounding tissues will also be moved at the same rate. A user may want to limit the maximum rate of movement of the bone or surrounding structures. Also of note is that certain portions of bone or tissue may move at different rates for a given distraction rate. For example, as the distal portion of the bone illustrated in FIG. 11 is moved to align with the proximal portion, a point on the distal portion of the bone near the osteotomy plane will move at a lower rate than a point on the distal portion of the bone farther away from the osteotomy plane because of the angle.

The LAF may default to the center of a moving fragment, one of the ends of the moving fragment, or anywhere else desired. If a user desires a LAF location other than the default location, he may change the location by changing the AP, lateral, and axial offset values. By setting the LAF location, a user may ensure that the maximum distraction rate applies to the LAF location. This ensures that a user may limit the maximum rate of movement of a particular portion of the bone or surrounding tissue.

The views of the second strut configuration screen 400 are displayed again on the LAF input screen 450. The user inputs LAF values for the AP offset, lateral offset, and axial offset. The user also enters a maximum distraction rate. The maximum distraction rate may represent, for example, the maximum, safest, or optimal amount of millimeters that the length of a strut can increase or decrease in a day, for example 1 mm/day. Based on the LAF input values and the maximum distraction rate, the user can initiate a calculation of the minimum amount of time it will take for the correction of the patient's deformed bone using the ring and strut configurations chosen in the previous steps. If the user is satisfied with the minimum correction time, he can move to the next step of generating the correction plan. If he is not satisfied, he can override the minimum correction time and enter a different value, and then continue to the step of generating the correction plan. For example, if the minimum correction time is initially output as 10 days, but the user (or a separate physician) will not be able to see the patient again for 14 days, the user may override the correction time to a value of 14 days. This potentially would allow for a more gradual correction plan, which may be of benefit.

On the correction plan generation screen 500, the user enters the date on which the user or patient will begin adjusting the fixation mechanism according to the correction plan. Once entered, the user commands the computer to generate a correction plan (FIG. 12). Once calculated, the correction plan 510 is displayed on the correction screen 500 (FIG. 13). The correction plan 510 can include, for example, the position and angle of each strut of the limb reconstruction frame for each day of the correction, along with the date and day number (e.g. first day, second day) of the correction plan 510. When the software is determining the deformity correction plan 510, an angle of the proximal portion of the bone 204 in relation to the distal portion of the bone 206 is utilized. In one embodiment, the software determines this angle based on the midlines of the two bone portions 204, 206. In another embodiment, the user may input the diameter of the bone. With the value of diameter of the bone, the software can base the value of the angle on the edges of the two bone portions 204, 206. Utilizing the outer edges of the bone portions 204, 206 provides for a more accurate correction plan 510.

The correction plan 510 may call for changing out one strut for a strut of a larger or smaller size during the period of correction. For example, a relatively small strut may be initially utilized between the reference and moving rings 305, 310. The angle and length of that small strut will be adjusted over time. At a certain point, the correction plan 510 may require to replace the relatively small strut with a relatively large strut because, for example, the relatively small strut may be close to reaching its maximum length. The software may provide an option to the user of changing out the relatively small strut or, instead, changing the point of connection of the small strut. By changing the point or points of connection of a strut, which may for example be a hole in the reference ring 305 and a hole in the moving ring 310, the length and position limitations of the strut are overcome. This option may be provided alternatively to changing out struts, or in addition, and applies to struts of all sizes.

The correction plan 510 may also show a relationship between positions of the struts and discrete user or patient actions. For example, if the correction plan 510 calls for a strut to be lengthened by 1 millimeter on the first day, the correction plan may indicate that the user or patient should increase the length of that strut four separate times, for example by 0.25 millimeters in the morning, 0.25 millimeters at noon, 0.25 millimeters in the evening and another 0.25 millimeters at night. Besides use as an instructional tool, the correction plan 510 also aids a physician or surgeon in monitoring the progress of the correction of the bone deformity, for example by checking at periodic intervals that the struts of the fixation frame are in the proper position as called for by the correction plan. In addition to the correction plan 510, the correction screen 500 may also include a simulation 520 of the correction. The user can view the simulation 520 to see what the progress of the correction should look like. The simulation 520 allows the user to see what the model bone, rings and struts will look like in one or more views on each day of the correction plan 510 or with each discrete correction made as called for by the correction plan. This helps the user ensure that the correction plan 510 is appropriate for the given case, and further aids the user in determining whether the correction is progressing according to the plan, as the user can compare the model of what the bone and fixation frame should look like to what the actual patient's bone and fixation frame look like on a given day.

The user has the option of viewing a report of all the pertinent details of a specific case in the study report screen 600, as seen in FIG. 14. The study report screen 600 is a comprehensive report of the case and can include information such as case details, parameter of the deformity definition, parameters for LAF input, parameters for the ring and strut configurations, and the complete correction plan, including the schedule of when one or more struts should be changed out for different struts, if necessary.

Figure 15:
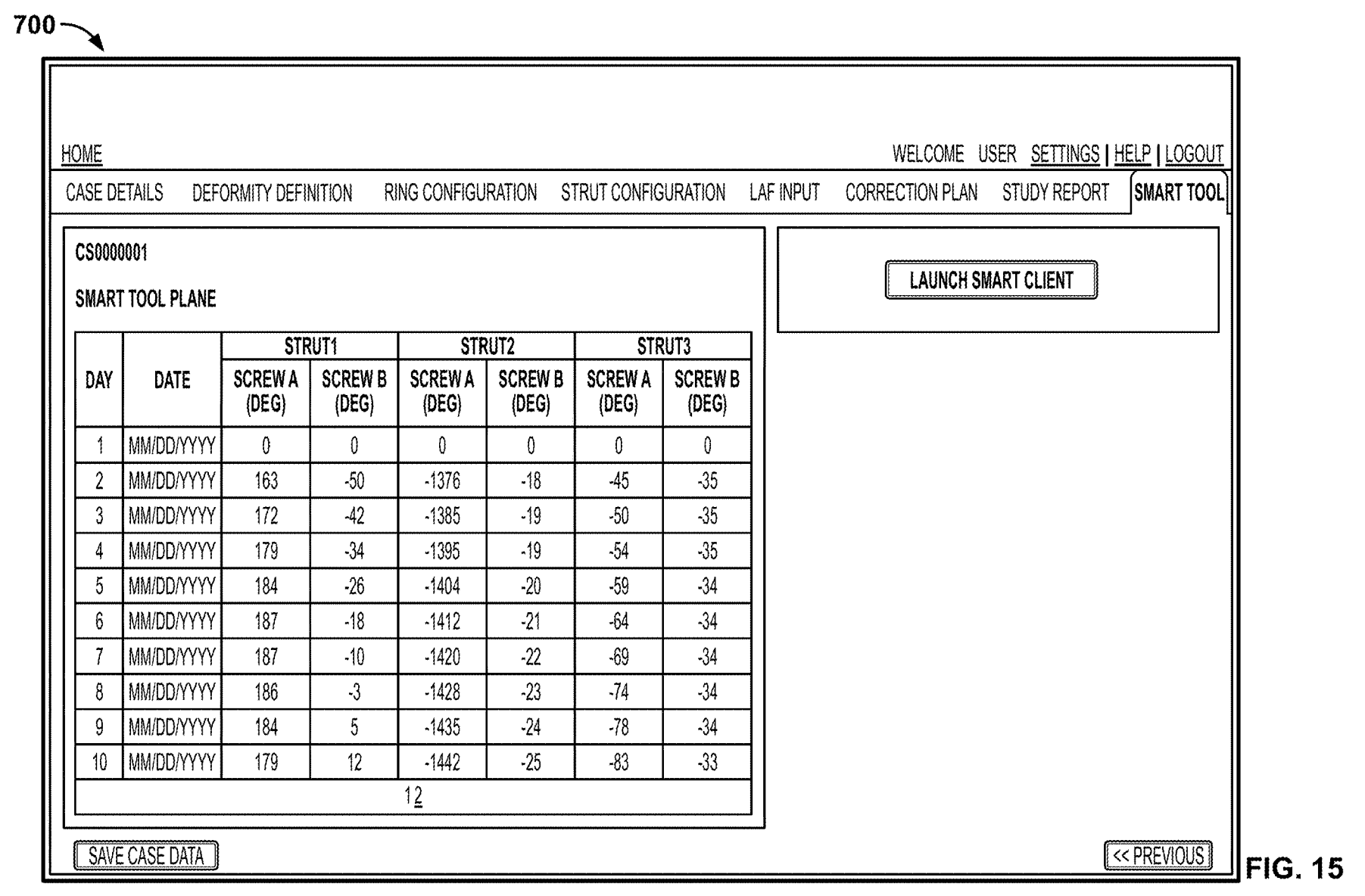

The user also has access to a smart tool screen 700 (FIG. 15). The smart tool screen 700 displays pertinent data for a smart tool plan and provides an option to launch a smart tool client to interface with the smart tool. Generally, a smart tool may be used in conjunction with the fixation frame and software described herein. The smart tool is an automated tool that a patient uses to perform the corrective fixation frame alterations described by the correction plan. For example, the smart tool may include a motor that rotates screws of the struts to lengthen the struts based on instructions downloaded from the software, which instructions correspond to the correction plan. The smart tool may limit the patient from changing the lengths of the struts in a manner other than described in the correction plan, and may communicate with the software and the case physician to reflect whether, or to what degree, the patient is following the correction plan. Such a smart tool is described more fully in U.S. application Ser. No. 13/167,101, the entire contents of which are hereby incorporated by reference herein.

As mentioned above, the application can be used in a post-op mode in addition or as an alternative to the pre-op mode. This mode can be used once the patient has already undergone surgery to attach the fixation frame to the deformed bone. The post-op mode can be used as an alternative to the pre-op mode, for example in cases in which time is limited and surgery must be performed without the benefit of the planning provided in the pre-op mode described above. Contrariwise, the pre-op mode may be especially useful in cases of a congenital deformity or in cases in which a deformity is stable, where planning time is available without risking the health of the patient.

In practice, the post-op mode should always be used, regardless of whether the pre-op mode is used. Even if the pre-op mode is used, a surgeon is likely to desire to confirm that the placement of rings and struts in surgery actually matches the pre-op plan.

In the post-op mode, the steps described above with reference to the login screen 102, home page 110, case details screen 120, and deformity definition screen 200 are the same (FIGS. 1-6). At the first ring configuration screen 250, the user would choose the post-op mode instead of the pre-op mode to continue in the post-op mode.

Figure 16:
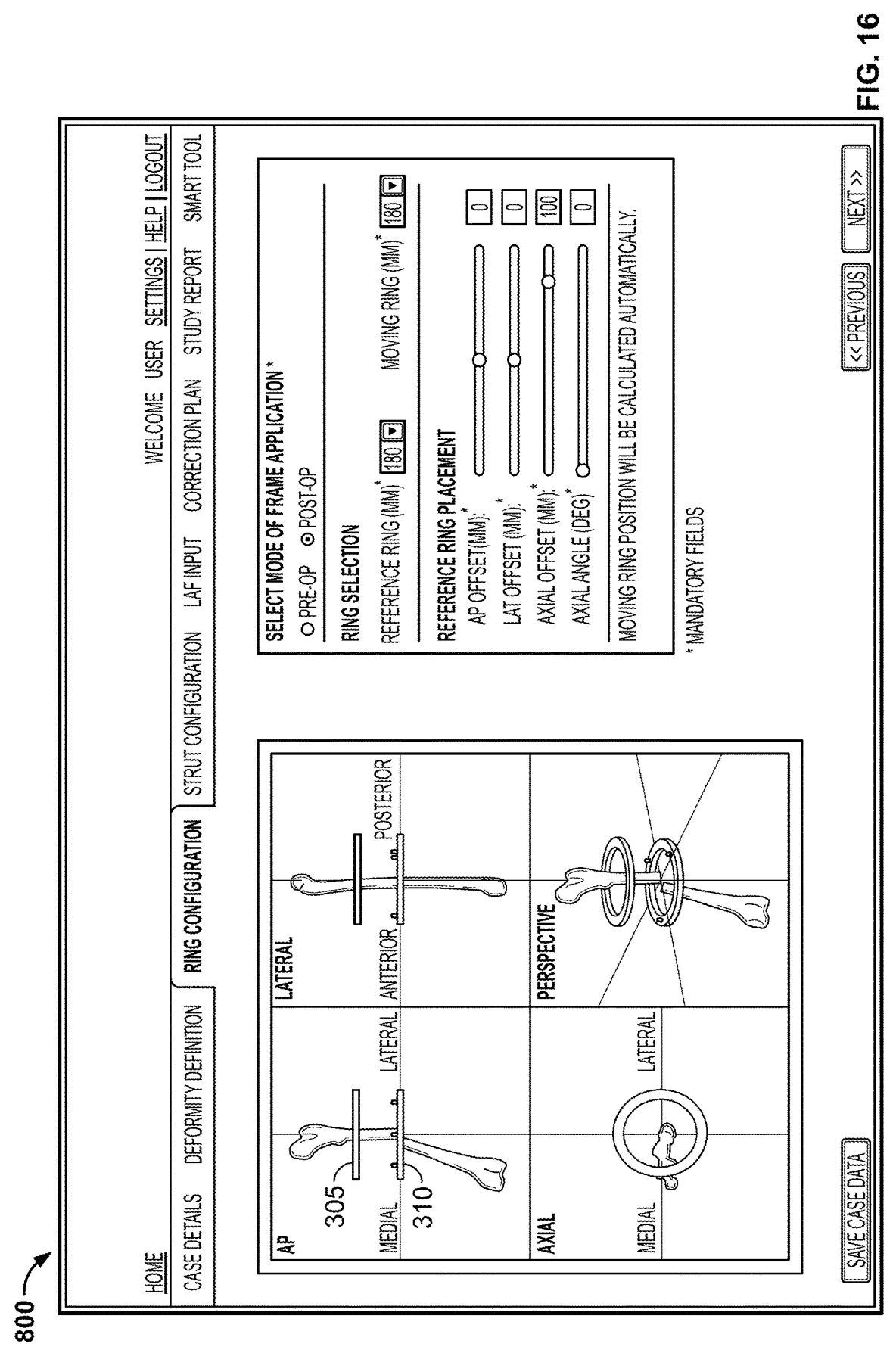

After selecting the post-op mode, the user proceeds to a post-op ring configuration screen 800 (FIG. 16). The user enters the sizes of both the reference ring 305 and the moving ring 310 as well as the position and orientation of the reference ring. These values are based on the sizes of the actual rings attached to the patient. For the reference ring, the user follows the same procedure as described for the pre-op ring configuration screen 300, either entering ring position parameters directly into the corresponding fields or by using a slide-bar to set the values. The user does not need to enter the positions of the moving ring 310, however, as this will be automatically determined during the next stages based on the positions of the struts.

Figure 17:
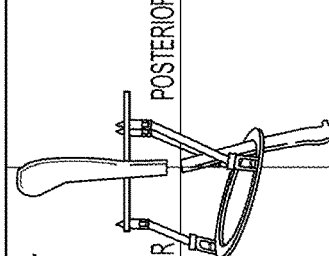
FIG. 17 illustrates a strut configuration screen of a post-operative mode of a deformity correction application.

The user proceeds to the post-op strut configuration screen 900 to enter the sizes and positions of the struts of the fixation frame attached to the patient during surgery (FIG. 17). The input values include the size of each strut, for example small, standard or large, the length of each strut, and the angle of each strut. The user may also have the option to enter the position along each ring that each strut is attached. For example, each ring may contain a plurality of through-holes for attachment of the struts, and each strut may be attached at recommended, predetermined through holes. These recommended, predetermined attachment through-holes are set as default attachment points in the software. However, if the physician is unable or unwilling to use the recommended, predetermined locations for strut attachment, he has the option to attach the struts at any other through-hole and the software can accommodate this modification. Again, these values are based on the actual fixation frame attached to the patient during surgery. Once the values are entered, the user can command the application to calculate the position of the moving ring 310 based on the position of the reference ring 305 and the struts. Once the moving ring position is calculated, the position and orientation fields for the AP, lateral, and axial axes populate with the calculated values. Once calculated, views of the fixation frame and model bone, for example AP, lateral, axial and perspective views, also update to reflect the calculated position and orientation of the moving ring. This provides additional confirmation to the surgeon that the model accurately represents the fixation frame of the case.

The remainder of the process from this point is the same as described with reference to the pre-op mode (FIGS. 12-15). The user advances through the LAF input screen 450 by entering LAF values and a minimum distraction rate to calculate a minimum correction time. The user then proceeds to the correction plan generation screen 500, enters the start date for the correction, and initiates the generation of a correction plan. As described with reference to the pre-op mode, the correction plan 510 and a simulation are then displayed on the correction screen 500. Again, the user can view a study report in the study report screen 600 and interface with a smart tool using the smart tool screen 700.

While the above description relates to creating a new case, the user may choose to open an existing case in the software if one exists. After logging in, the user can choose an existing case by, for example, searching for an existing case or choosing from a list of existing cases 114 (FIG. 2). After opening the existing case, the user is taken to an existing case screen 1000 (FIG. 18) that shows patient details and the existing cases for the patient. From this screen, the user can choose to open a particular study of interest, create a new case for the patient, or view a report of the case summary. If the user opens the existing case, he is able to review or edit the case using the procedures described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of planning for correcting a deformed bone of a patient, the method comprising:
   prior to coupling an external fixation frame to the patient:
      displaying on a first display device a first representation of a first segment of the deformed bone and a first representation of a second segment of the deformed bone;
      manipulating a position of the first representation of the first segment relative to a position of the first representation of the second segment to match an actual position of the first segment of the deformed bone with respect to an actual position of the second segment of the deformed bone;
      displaying a first model of a first fixation ring of the external fixation frame on the first display device overlying the first representation of the first segment in a first ring position;
      displaying a first model of a second fixation ring of the external fixation frame on the first display device overlying the first representation of the second segment in a second ring position;
      determining, based on the first ring position and the second ring position, at least one combination of sizes of a plurality of model struts to connect the first models of the first and second fixation rings; and
      generating a first pre-operative correction plan; and
   after (i) coupling the first fixation ring of the external fixation frame to the first segment of the deformed bone in an actual first ring position, (ii) coupling the second fixation ring of the external fixation frame to the second segment of the deformed bone in an actual second ring position, and (iii) coupling the first fixation ring to the second fixation ring with a plurality of struts having actual sizes and positions:
      displaying on a second display device a second representation of the first segment of the deformed bone and a second representation of the second segment of the deformed bone;
      manipulating a position of the second representation of the first segment relative to a position of the second representation of the second segment to match the actual position of the first segment of the deformed bone with respect to the actual position of the second segment of the deformed bone;

displaying a second model of the first fixation ring on the second display device overlying the second representation of the first segment so that a position of the second model of the first fixation ring matches the actual first ring position;

displaying a plurality of model struts on the second display, the plurality of model struts having sizes and positions that match the actual sizes and positions of the plurality of struts coupling the first fixation ring to the second fixation ring;

determining the actual second ring position based on the position of the second model of the first fixation ring and the sizes and positions of the plurality of model struts;

displaying a second model of the second fixation ring on the second display device overlying the second representation of the second segment, the second model of the second fixation ring having the determined actual second ring position; and generating a second post-operative correction plan.

2. The method of claim 1, wherein the second display device is the first display device.

3. The method of claim 1, wherein the first representation of the first segment of the deformed bone and the first representation of the second segment of the deformed bone are included in a first x-ray image in an anterior-posterior view or a lateral view.

4. The method of claim 3, wherein during the step of manipulating the position of the first representation of the first segment relative to the position of the first representation of the second segment, the first representation of the first segment and the first representation of the second segment are both overlaid on the first x-ray image.

5. The method of claim 4, wherein the first x-ray image is at least partially transparent.

6. The method of claim 3, wherein the second representation of the first segment of the deformed bone and the second representation of the second segment of the deformed bone are included in a second x-ray image in an anterior-posterior view or a lateral view.

7. The method of claim 6, wherein during the step of manipulating the position of the second representation of the first segment relative to the position of the second representation of the second segment, the second representation of the first segment and the second representation of the second segment are both overlaid on the second x-ray image.

8. The method of claim 7, wherein the second x-ray is at least partially transparent.

9. The method of claim 7, wherein the step of manipulating the position of the second representation of the first segment relative to the position of the second representation of the second segment includes at least one of rotating, zooming, or repositioning the second x-ray image.

10. The method of claim 3, wherein the step of manipulating the position of the first representation of the first segment relative to a position of the first representation of the second segment includes at least one of rotating, zooming, or repositioning the first x-ray image.

11. The method of claim 1, further comprising selecting a desired one of the at least one combination of sizes of the plurality of model struts to connect the first models of the first and second fixation rings.

12. The method of claim 11, wherein the plurality of struts having actual sizes and positions that are used to couple the first fixation ring to the second fixation ring correspond to the selected desired one of the at least one combination of sizes of the plurality of model struts.

13. The method of claim 1, wherein the step of manipulating the position of the first representation of the first segment relative to the position of the first representation of the second segment includes one of entering numerical values into an input box and moving a slide-bar corresponding to the numerical values.

14. The method of claim 1, wherein the step of manipulating the position of the second representation of the first segment relative to the position of the second representation of the second segment includes one of entering numerical values into an input box and moving a slide-bar corresponding to the numerical values.

15. The method of claim 1, wherein the first fixation ring has a size corresponding to the size of the first model of the first fixation ring.

16. The method of claim 15, wherein the second fixation ring has a size corresponding to the size of the first model of the second fixation ring.

17. The method of claim 1, wherein the actual first ring position matches the first ring position.

18. The method of claim 17, wherein the actual second ring position matches the second ring position.

\* \* \* \* \*